US010857348B2

(12) United States Patent
Greger et al.

(10) Patent No.: US 10,857,348 B2
(45) Date of Patent: Dec. 8, 2020

(54) COMPLIANT DEVICES FOR NEURAL PROSTHETIC DEVICES

(71) Applicant: Arizona Board of Regents on Behalf of Arizona State University, Scottsdale, AZ (US)

(72) Inventors: Bradley Greger, Phoenix, AZ (US); Mark Mahan, Salt Lake City, UT (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 1272 days.

(21) Appl. No.: 15/044,469

(22) Filed: Feb. 16, 2016

(65) Prior Publication Data

US 2016/0256062 A1   Sep. 8, 2016

Related U.S. Application Data

(60) Provisional application No. 62/128,442, filed on Mar. 4, 2015.

(51) Int. Cl.
*A61N 1/05* (2006.01)
*A61N 1/372* (2006.01)
*A61B 5/00* (2006.01)
*A61B 5/04* (2006.01)
*A61F 2/72* (2006.01)

(52) U.S. Cl.
CPC ........ *A61N 1/0551* (2013.01); *A61B 5/04001* (2013.01); *A61B 5/685* (2013.01); *A61B 5/6877* (2013.01); *A61N 1/37264* (2013.01); *A61F 2/72* (2013.01)

(58) Field of Classification Search
CPC .. A61N 1/0551; A61N 1/0529; A61N 1/0534; A61B 5/04001; A61B 5/685; A61B 5/6868; A61B 5/6877; A61B 5/04888; A61B 2562/04; A61B 2562/028

USPC ......................................................... 600/377
See application file for complete search history.

(56) References Cited

U.S. PATENT DOCUMENTS

| | | | | |
|---|---|---|---|---|
| 5,143,089 A * | 9/1992 | Alt | ....................... | A61N 1/0587 600/374 |
| 5,868,740 A * | 2/1999 | LeVeen | .............. | A61B 18/1477 606/41 |
| 6,171,239 B1 * | 1/2001 | Humphrey | ........... | A61B 5/0482 600/372 |
| 6,456,866 B1 | 9/2002 | Tyler et al. | | |

(Continued)

OTHER PUBLICATIONS

Branner et al., Selective Stimulation of Cat Sciatic Nerve Using an Array of Varying-Length Microelectrodes., Journal of Neurophysiology, Apr. 2001, 85(4):1585-1594.

(Continued)

*Primary Examiner* — Lee S Cohen
*Assistant Examiner* — Erin M Cardinal
(74) *Attorney, Agent, or Firm* — Quarles & Brady LLP

(57) ABSTRACT

A device for neural prosthetics is disclosed. The device comprises arrays of micro-wires and a control unit. The control unit connects to and communicates with the micro-wires. The ends of the micro-wires serve as microelectrodes. The microelectrodes are in contact with neural tissue. The micro-wires are covered in sheaths made of conformal material. The ends of the micro-wires protrude beyond the ends of the sheaths. This allows the electrodes to be individually positioned on the neural tissue.

17 Claims, 2 Drawing Sheets

(56) References Cited

U.S. PATENT DOCUMENTS

| | | | |
|---|---|---|---|
| 8,630,711 B1 | 1/2014 | Wark et al. | |
| 2004/0133118 A1* | 7/2004 | Llinas | A61B 5/04001 600/544 |
| 2005/0090756 A1* | 4/2005 | Wolf | A61N 1/08 600/546 |
| 2006/0149226 A1* | 7/2006 | McCullagh | A61B 18/148 606/41 |
| 2007/0088417 A1* | 4/2007 | Schouenborg | A61N 1/0529 607/116 |
| 2008/0208280 A1 | 8/2008 | Lindenthaler et al. | |
| 2009/0248113 A1* | 10/2009 | Nimer | A61N 1/05 607/60 |
| 2010/0114272 A1* | 5/2010 | Haidarliu | A61B 5/04001 607/115 |
| 2011/0054612 A1* | 3/2011 | Dehnad | A61L 31/16 623/16.11 |
| 2013/0085361 A1* | 4/2013 | Mercanzini | A61B 5/04001 600/377 |
| 2014/0330354 A1* | 11/2014 | Shelton | A61N 1/0551 607/116 |
| 2015/0133761 A1 | 5/2015 | Vetter et al. | |
| 2017/0007824 A1* | 1/2017 | Gardner | A61B 5/6877 |

OTHER PUBLICATIONS

Rajaraman, Micromachining Techniques for Realization of Three-Dimensional Microelectrode Arrays., Nanotechnology and neuroscience: nano-electronic, photonic and mechanical neuronal interfacing (eds. Vittorio et al.), 2014, Chapter 5, pp. 135-182.

Vetter et al., Chronic Neural Recording Using Silicon-Substrate Microelectrode Arrays Implanted in Cerebral Cortex, IEEE Transactions on Biomedical Engineering, Jun. 2004, 51(6):896-904.

Yoshida et al., Development of Chronic Longitudinal Intrafascicular Electrodes, Proceedings of 18th Annual International Conference of the IEEE Engineering in Medicine and Biology Society, 1996, vol. 1., pp. 373-374.

Leventhal et al., Subfascicle stimulation selectivity using a FINE, Proceedings of the 22nd Annual International Conference of the IEEE Engineering in Medicine and Biology Society (Cat. No. 00CH37143), 2000, vol. 3., pp. 1610-1612.

* cited by examiner

COMPLIANT DEVICES FOR NEURAL PROSTHETIC DEVICES

CROSS-REFERENCE TO RELATED APPLICATIONS

This application claims the benefit of U.S. Provisional Patent Application No. 62/128,442, filed Mar. 4, 2015, which is incorporated herein by reference as if set forth in its entirety.

STATEMENT REGARDING FEDERALLY SPONSORED RESEARCH

Not applicable.

BACKGROUND

Neural prostheses are devices that can substitute motor, sensory, or cognitive functions of damaged nerves. These devices need to interact with neural tissue of the patient, such as recording neurophysiological signals from a nerve or stimulating a nerve. For this purpose, the material of the devices should be compliant so the devices can move smoothly with the nerve or muscle and the communication signals between the devices and the nerve should be maximized. Other peripheral nerve interfaces—including, without limitation, the Utah Slanted Electrode, the Michigan Probe by NeuroNexus, longitudinal intrafascicular electrodes (LIFE), and flat interface nerve electrodes—fail in at least one of these two regards. Some of them do not sample a complete cross-section of the nerve and therefore limit the amount of information recorded from the nerve. Moreover, penetrating electrodes enter the nerve at a right angle, which subject the nerve or the electrode to injury as the nerve slides to accommodate joint movement. Some are made of non-compliant and brittle material that are subject to failure in real-world use. An improved neural prosthesis that is compliant and durable, tolerates normal nerve biomechanical changes, and has an electrode distribution that maximizes the information transferred to and from the neural tissue is needed.

SUMMARY

The present disclosure overcomes the aforementioned drawbacks by providing a device for neural prosthetics that has critical portions made of neurally conformal material and samples nervous system information across a complete cross-section of the interfacing nerve. The device comprises arrays of micro-wires and a control unit. The control unit connects to and communicates with the micro-wires. The ends of the micro-wires serve as microelectrodes that are placed into contact with neural tissue. The micro-wires are covered in sheaths made of conformal material. The ends of the micro-wires comprising the microelectrodes protrude beyond the ends of the sheaths. This allows the microelectrodes to be individually positioned on the neural tissue. In one configuration, the conformal material is silicone elastomers.

In one configuration, the micro-wires are in two arrays, one for recording electrophysiological signals from one neural tissue and the other for sending micro-stimulation signals to another neural tissue. The capacitive coupling between the two arrays of micro-wires can be minimized. For example, the array for micro-stimulation is wrapped in a spiral around the array for recording signals. In another example, the two arrays are in different lengths.

In one configuration, each of the arrays has multiple tufts of micro-wires and each tuft is positioned to maximize the recording and micro-stimulation of different elements of the neural tissue.

The device is distinguished from other neural interfaces in the technique of implant. The device is to be implanted in a nerve after opening the epineurium of the nerve, such that the wires are placed in direct contact with the perineurium lining the fascicles of the nerve. The intent of the technique of implantation is to minimize damage and trauma to the nerve. Currently available electrodes, i.e., LIFE and USEA, depend upon sharp penetration through the epineurium without visualizing the fascicles of the nerve. These electrodes are designed to be placed either with blind passage of a needle through the nerve (LIFE) or use of a controlled impact (USEA) to the nerve. In contrast, the presently described electrode is to be implanted after surgical opening of the outer layer of the nerve (epineurium) and the fascicles of the nerve can be visualized. The conducting fibers of the presently described electrode then measure electrical activity adjacent to the nerve fibers, but without sharp or concussive penetration into the endoneurial components of the nerve.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present application discloses a device for neural prosthetics that provides a large number of microelectrodes to interface in a spatially distributed manner with a peripheral nerve using mechanically compliant materials that will move with the nerve. Disclosed methods of using the device provide for the device to be implanted with a technique that limits injury to the nerve. The microelectrode distribution across the complete cross-section of the peripheral nerve maximizes the information transferred to and from neural tissue. Devices used for neural prosthetics need to interact with neural tissue of the patient to control the neural tissue and substitute its motor, sensory, visceral or cognitive functions. Because of the interactions, such devices are also called interfaces. As described herein, compliant devices of this disclosure maximize information transferred to and from neural tissue.

Interfaces often target peripheral nerves, which connect the brain and the spinal cord to the rest of the body. Peripheral nerves can be attached to neural prostheses or interfaces. These nerves are typically not protected by bone; they run within or along the muscle tissue of the limbs and move relative to other tissue. In addition, peripheral nerves are roughly cylindrical in shape. Nerves are covered in multiple layers of thick connective tissues, which partially insulates and reduces resolution of the electrical signals of the hundreds to thousands of nerve fibers (axons) contained within the nerve. The nerve fibers are organized into discrete cables (fascicles) within the nerve, which are bound by a thin connective tissue membrane (perineurium). Entry through this membrane, i.e., perineurium, inevitably leads to injury and destruction of the nerve fibers.

The devices disclosed in the present application may be configured to non-destructively sample the complete cross-section of the nerve to maximize information transferred to and from the nerve. The electrode provides a novel fine wire interface that does not penetrate the perineurium.

Figure 1:
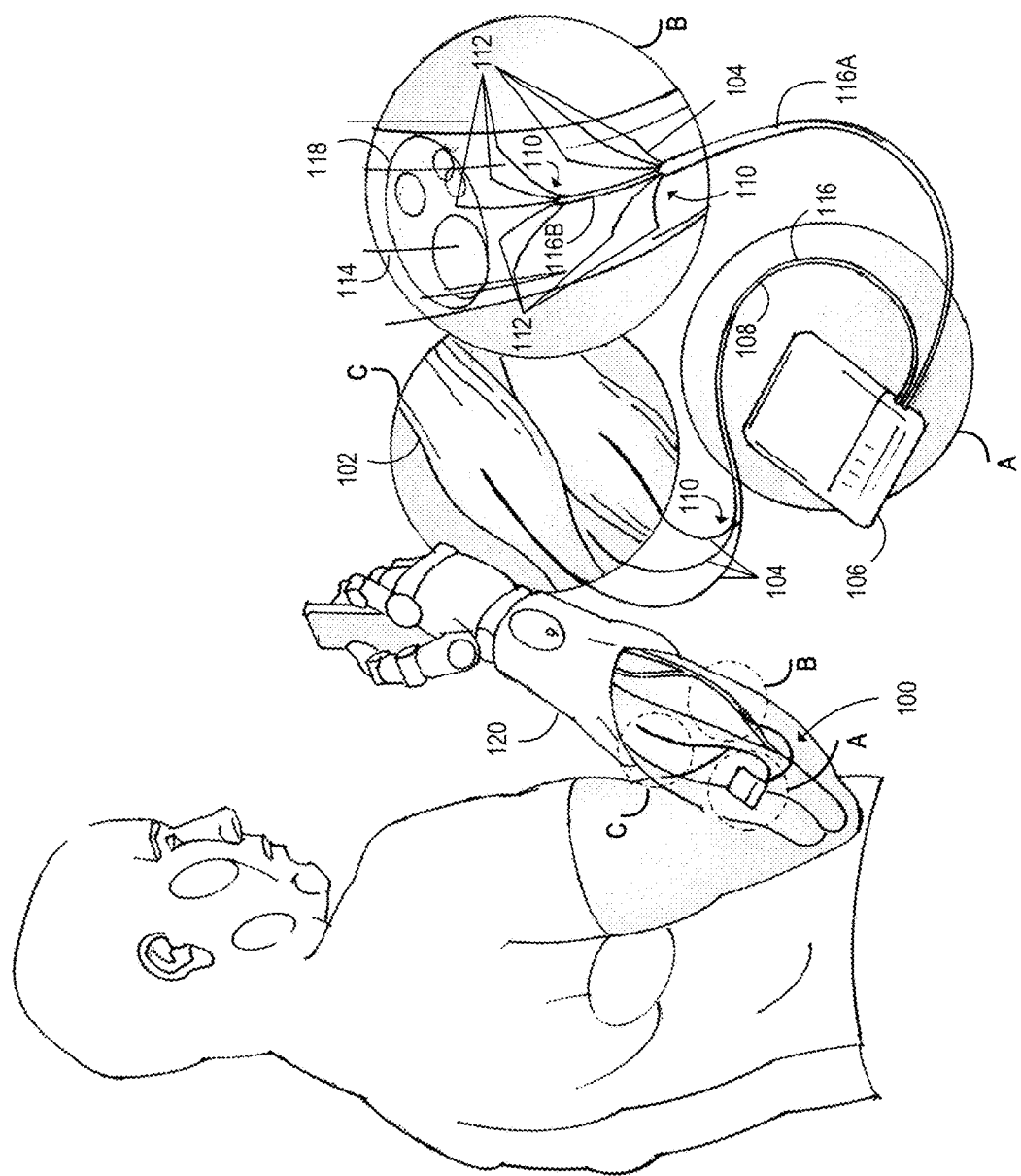
FIG. 1 is a schematic diagram of a device configured in accordance with the present application.

Referring now to FIG. 1, a schematic diagram of a device 100 in accordance with the present application is provided. Nerves, particularly peripheral nerves, will benefit from installation of the device 100 as described, but a person skilled in the art would appreciate that the device 100 can also be implemented on other neural tissue in accordance with the present application. FIG. 1 and its insets A (showing control unit 106), B (showing microelectrodes 112 distributed within a peripheral nerve 114), and C (showing tufts 110 of micro-wires 104 inserted into neural tissue 102 for muscle control) are not to scale. The device 100 includes one or more arrays 108 of a plurality of micro-wires 104 attached at the proximal end and in electrical communication with a control unit 106. The control unit 106 may be in wired or wireless communication with a prosthetic 120 in order to transmit and receive data, such as recorded neural activity and desired muscle stimuli. The micro-wires 104 of each array 108 may be bunched together and covered in at least one sheath 116 made of conformal material that moves with the nerve to maximize robustness and maintain signal stationarity. For example, the sheaths 116 may be made of silicone elastomers. This allows the devices to be long-term chronic neural interfaces for neural prosthetic applications.

The sheath 116 of each array 108 may extend from the control unit 106 to a position approximate the attachment of the micro-wires 104 to the neural tissue (e.g., peripheral nerve 114). The distal ends of the micro-wires 104 protrude beyond the end of the sheath 116 for the array 108. The micro-wires 104 then diverge at the projecting portions, forming a tuft 110 of micro-wire 104 ends that are held together by the sheath 116 and, essentially, spread out. The distal end of each micro-wire 104 serves as a microelectrode 112 that may be individually positioned in a suitable location to make contact with the peripheral nerve 114. Multiple tufts 110 can be used in a single array of micro-wires 104 held together by the sheath 116 and positioned at different neural elements of neural tissue 102. The device 100 can provide a large number of microelectrodes 112 to interface with a peripheral nerve in a spatially distributed manner. In aggregate, the microelectrodes 112 can spatially sample the entire cross-section 118 of a peripheral nerve 114.

In one embodiment, the device 100 can be comprised of at least two arrays 108 of micro-wires 104, at least one for electrophysiological recording and at least one other for micro-stimulation. In one configuration, the microelectrodes 112 detect neurophysiological signals from the peripheral nerve 114 and transmit the signals to the control unit 106 through the micro-wires 104. In another configuration, the control unit 106 sends micro-stimulation signals via micro-wires 104 and their microelectrodes 112 to neural tissue 102, where the neural tissue 102 controls muscle movement. To minimize the capacitive coupling between the array 108 carrying the recording signals and the array 108 carrying the micro-stimulation signals, the arrays 108 for recording may be different lengths from the arrays 108 for micro-stimulation. In another arrangement to minimize the capacitive coupling, the arrays for micro-stimulation may be wrapped in a spiral around the arrays for recording, or vice versa.

In another configuration, one of the arrays 108, including its sheath 116B, may be contained within the sheath 116A of another array 108, as illustrated in inset B. The "outer" sheath 116A may be shorter than the "inner" sheath 116B, such that a first of the tufts 110 is formed by the outer sheath 116A proximally from a second of the tufts 110 formed by the inner sheath 116B. The microelectrodes 112 of each array 108 are thus spatially separated, enabling complete-cross-section 118 sampling of the peripheral nerve 114 at two locations thereon.

In another configuration, each tuft 110 in one array 108 may be positioned at a different element of neural tissue 102 so to maximize micro-stimulation, as illustrated in inset C.

The desired locations of the microelectrodes are adjacent and circumferential to specific fascicles of the nerve. Once the electrode tips on all wires are placed to spatially sample the nerve at desired locations of the nerve, the entire array can be back-loaded into a stylet or cannula. The stylet or cannula provides the necessary rigidity and allows the array to be inserted into the nerve. Once the array is inserted, the stylet or cannula can be pulled out leaving the microelectrode array in place and spread out in the entire cross-section of the nerve.

Figure 2:
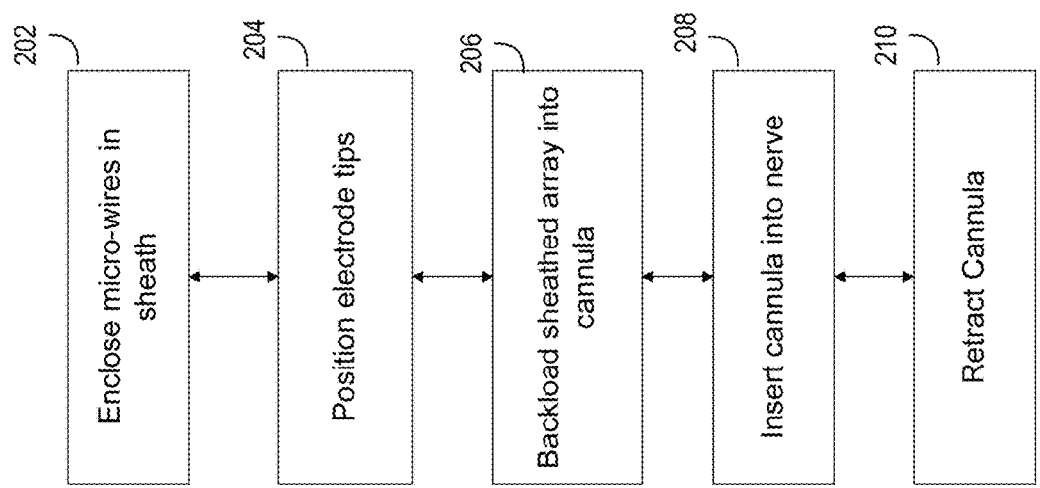
FIG. 2 is a flowchart illustrating a method for inserting microelectrodes into a nerve.

Referring now to FIG. 2, a flowchart depicting example procedures to insert microelectrodes into a nerve is provided. In step 202, micro-wires are enclosed in a sheath. In step 204, the electrode tips—microelectrodes—are placed at desired locations of the nerve. In step 206, the sheathed micro-wire array is backloaded into a cannula. In step 208, the cannula is inserted into the nerve. Afterwards, in step 210, the cannula is retracted from the nerve, leaving the microelectrodes in place.

The devices disclosed in the present application can be integrated into prosthetic limbs to provide neural control and receive sensory feedback from the prosthetic limbs.

The present invention has been described in terms of one or more preferred embodiments, and it should be appreciated that many equivalents, alternatives, variations, and modifications, aside from those expressly stated, are possible and within the scope of the invention.

We claim:

1. A device for neural prosthetics, the device comprising:
a control unit; and
arrays of micro-wires, wherein:
  each of the arrays is covered by at least one sheath of a plurality of sheaths each made of conformal material, wherein each of the micro-wires of the array includes a proximal end electrically connecting the micro-wire to the control unit, and a distal end that extends out beyond an end of at least one of the sheaths covering the array;
  the distal end of each of the micro-wires defines a corresponding microelectrode of a plurality of microelectrodes each communicating with the control unit via a corresponding micro-wire in one of the arrays;
  each of the plurality of microelectrodes is configured to be placed in contact with neural tissue and individually positioned on the neural tissue, the corresponding microelectrodes of a first of the arrays of micro-wires being further configured to be placed on a perineurium of a peripheral nerve of a patient without sharp or concussive penetration into endoneurial components of the peripheral nerve;
wherein the arrays are configured to cooperate to simultaneously:
detect and record electrophysiological signals from the neural tissue; and
apply stimulation to the neural tissue; and
wherein the at least one sheath covering each of the arrays is configured to conform to movement of the peripheral nerve on which the device is implanted such that the corresponding microelectrodes are prevented from entering the perineurium of the peripheral nerve after implantation of the device on the perineurium.

2. The device of claim 1, wherein
the corresponding microelectrodes of the micro-wires in the first array are configured to detect the electrophysiological signals from first neural tissue of the peripheral nerve and transmit the electrophysiological signals to the control unit, the control unit recording the electrophysiological signals, and
the corresponding microelectrodes of the micro-wires in a second of the arrays of micro-wires receive micro-stimulation signals from the control unit and apply the stimulation according to the micro-stimulation signals to second neural tissue that controls a muscle.

3. The device of claim 2, wherein each of the arrays has multiple tufts of micro-wires and each tuft is positioned to maximize the recording or the micro-stimulation of different elements of the first or second neural tissue.

4. The device of claim 2, wherein capacitive coupling between the first and second arrays is minimized.

5. The device of claim 4, wherein the second array of micro-wires is wrapped in a spiral around the first array of micro-wires.

6. The device of claim 4, wherein the first array of micro-wires are in lengths different from those of the second array of micro-wires.

7. The device of claim 1, wherein the conformal material is silicone elastomers.

8. The device of claim 1, wherein the corresponding microelectrodes of the micro-wires in the first array are configured to be positioned to, in aggregate, form an interface with the peripheral nerve, the interface sampling an entire cross-section of the peripheral nerve at a first location comprising the neural tissue.

9. The device of claim 8, wherein to form the interface, the corresponding microelectrodes of the micro-wires in the first array are configured to be spatially distributed in contact with one or more perineuria of the peripheral nerve without penetrating the perineuria.

10. The device of claim 1, wherein each of the corresponding microelectrodes of the micro-wires in the first array is configured to be implanted by placing the corresponding microelectrode in direct contact with the perineurium through a surgical opening in the epineurium.

11. The device of claim 1, wherein the micro-wires in the first array are bunched and held together by a first sheath of the plurality of sheaths, and diverge from each other upon extending beyond the distal end of the first sheath to form a tuft that spatially distributes the corresponding microelectrodes, the first sheath and the micro-wires of the first array cooperating to:
allow the individual positioning of the corresponding microelectrodes to produce a distribution of the tuft in which the corresponding microelectrodes are placed at desired locations of the peripheral nerve upon implantation of the device; and
maintain the tuft in the distribution as the first array is backloaded into a cannula.

12. A device for neural prosthetics, the device comprising:
a control unit;
a plurality of sheaths each made of conformal material; and
first and second arrays of micro-wires, wherein:
each of the arrays is covered by at least one of the plurality of sheaths, wherein each of the micro-wires of the array includes a proximal end electrically connecting the micro-wire to the control unit, and a distal end that extends out beyond an end of the at least one of the sheaths covering the array;
the distal end of each of the micro-wires defines a corresponding microelectrode of a plurality of microelectrodes each communicating with the control unit via a corresponding micro-wire in one of the arrays;
each of the plurality of microelectrodes is configured to be placed in contact with one or more neural tissues and individually positioned in contact with a corresponding intact perineurium of a plurality of perineuria of peripheral nerves of the one or more neural tissues;
the corresponding microelectrodes of the first array are configured to detect electrophysiological signals from the one or more neural tissues and transmit the electrophysiological signals to the control unit, the control unit recording the electrophysiological signals; and
the corresponding microelectrodes of the second array are configured to receive micro-stimulation signals from the control unit and apply stimulation to the neural tissue according to the micro-stimulation signals; and
wherein the at least one sheath covering each of the arrays is configured to conform to movement of the peripheral nerve on which the device is implanted such that microelectrodes corresponding to each of the arrays are prevented from entering the perineurium of the peripheral nerve after implantation of the device.

13. The device of claim 12, wherein each of the plurality of microelectrodes is configured to be individually positioned for implantation through a surgical opening of an epineurium of the peripheral nerve.

14. The device of claim 13, wherein the corresponding microelectrodes of the first array are configured to, upon implantation of the device, form an interface with the peripheral nerve that samples an entire cross-section of the peripheral nerve.

15. The device of claim 12, wherein the corresponding microelectrodes of the first array are configured to detect the electrophysiological signals of peripheral nerves of a first of the one or more neural tissues, and the corresponding microelectrodes of the second array are configured to receive the micro-stimulation signals from the control unit and apply the stimulation to peripheral nerves of a second of the one or more neural tissues that control muscle movement.

16. The device of claim 12, wherein the plurality of sheaths comprises:
a first sheath substantially covering the first array of the micro-wires; and a second sheath substantially covering at least the second array of the micro-wires.

17. The device of claim 16, wherein the second array of the micro-wires is wrapped in a spiral around the first sheath and the first array of the micro-wires.

\* \* \* \* \*